(12) United States Patent
Awad et al.

(10) Patent No.: US 9,789,146 B1
(45) Date of Patent: Oct. 17, 2017

(54) SYNTHESIS OF ADANSONIA DIGITATA NANOPARTICLES

(71) Applicant: KING SAUD UNIVERSITY, Riyadh (SA)

(72) Inventors: Manal Ahmed Gasmelseed Awad, Riyadh (SA); Awatif Ahmed Hendi, Riyadh (SA); Khalid Mustafa Osman Ortashi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/452,688

(22) Filed: Mar. 7, 2017

(51) Int. Cl.
*A61K 36/185* (2006.01)
*A61K 9/51* (2006.01)

(52) U.S. Cl.
CPC .......... *A61K 36/185* (2013.01); *A61K 9/5138* (2013.01); *A61K 9/5161* (2013.01); *A61K 9/5192* (2013.01); *A61K 2236/333* (2013.01); *A61K 2236/39* (2013.01); *A61K 2236/51* (2013.01)

(58) Field of Classification Search
CPC .. A61K 36/185; A61K 9/5192; A61K 9/5161; A61K 9/5138; A61K 2236/51; A61K 2236/333; A61K 2236/39
See application file for complete search history.

(56) References Cited

U.S. PATENT DOCUMENTS 8,168,225 B2    5/2012  Casaña Giner et al.

OTHER PUBLICATIONS

Elsaid, "The Effect of Seeds and Fruit Pulp of *Adansonia digitate* L. (Baobab) on Ehrlich Ascites Carcinoma," Food and Nutrition Sciences, 2013, 4, pp. 38-46.

*Primary Examiner* — Trevor Love
(74) *Attorney, Agent, or Firm* — Richard C. Litman (57) ABSTRACT

A method of preparing *Adansonia digitata* nanoparticles includes dissolving *Adansonia digitata* plant powder in an organic solvent to form a solution; spraying the solution in boiling water while applying ultrasonic energy to form a mixture; and stirring the mixture for at least about 15 minutes at a speed of about 200-800 rpm to obtain the *Adansonia digitata* nanoparticles.

5 Claims, 10 Drawing Sheets

SYNTHESIS OF ADANSONIA DIGITATA NANOPARTICLES

BACKGROUND OF THE INVENTION

1. Field of the Invention

The present invention relates to bio-nanotechnology and, particularly, to a method of synthesizing *Adansonia digitata* non-metal nanoparticles for use as anti-cancer and antimicrobial agents.

2. Description of the Related Art

*Adansonia digitata* plant belongs to the family Malvaceae, which is a large tree indigenous to Africa but is also found in many other countries. *Adansonia digitata* is commonly known as the baobab tree. Traditionally, the baobab fruit pulp is dissolved in water or milk and is used as a drink or sauce for food in Africa. The baobab fruit pulp and powdered seeds are used for the treatment of diarrhea and dysentery in India. The high content of Vitamin C in the fruit pulp is recommended for pregnant women. In recent times, scientists have demonstrated different activities of the pulp, including hepatoprotective, antimicrobial, antiviral, antioxidant, antidiarrheal, hypoglycemic, anti-inflammatory, and antioxidant activities.

Thus, a method of producing nanoparticles of *Adansonia digitata* and carrier encapsulated *Adansonia digitata* nanoparticles solving the aforementioned problems is desired.

SUMMARY OF THE INVENTION

A method of preparing *Adansonia digitata* nanoparticles includes the steps of dissolving *Adansonia digitata*, e.g., *Adansonia digitata* fruit powder, in an organic solvent to form a solution; adding the solution to boiling water under ultrasonic conditions to form a mixture; and stirring the mixture at a temperature of about 24° C. and a speed of about 200 rpm to about 800 rpm to obtain *Adansonia digitata* nanoparticles. The organic solvent can be at least one of methanol, ethanol, dichloromethane, and chloroform.

A method of synthesizing carrier encapsulated *Adansonia digitata* nanoparticles includes the steps of dissolving *Adansonia digitata* plant powder and a carrier in an organic solvent to form a solution; adding the solution into water containing polyvinyl alcohol to form a mixture; and homogenizing the mixture at a temperature of about 24° C. and at a speed of about 22,000 rpm to obtain encapsulated *Adansonia digitata* nanoparticles.

A method of treating cancer can include administering an effective amount of *Adansonia digitata* nanoparticles or encapsulated *Adansonia digitata* nanoparticles to a patient in need thereof.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

A method of preparing *Adansonia digitata* nanoparticles includes dissolving *Adansonia digitata* plant powder, e.g., a powder formed from *Adansonia digitata* fruit pulp, seeds, leaves, flowers, roots, and/or bark, in an organic solvent to form a solution; adding the solution to boiling water under ultrasonic conditions to form a mixture; and stirring the mixture at room temperature for about ten minutes and a speed of about 200 rpm to about 800 rpm to obtain *Adansonia digitata* nanoparticles. Ultrasonic conditions can include applying ultrasonic energy of about 100 W at a frequency of about 30-60 kHz, e.g., about 30 kHz. Ultrasonication may be performed using an ultrasonic bath or an ultrasonic probe. The mixture can be sonicated for about 10 minutes to about 20 minutes prior to stirring. The organic solvent can be at least one of methanol, ethanol, dichloromethane, and chloroform. The solution can be sprayed into the boiling water dropwise with a flow rate of 0.2 mL/min for about five minutes. For example, about 3 mL of the solution can be added to about 100 mL of the boiling water.

The *Adansonia digitata* nanoparticles prepared according to the inventive method can possess a mean diameter in the range of from about 50 nm to about 300 nm, e.g., about 230 nm. The *Adansonia digitata* nanoparticles can have spherical, spheroidal, elongated spherical, rod-shaped, and/or faceted shapes.

A method of synthesizing carrier encapsulated *Adansonia digitata* nanoparticles includes dissolving *Adansonia digitata*, e.g., *Adansonia digitata* nanoparticle powder, and an appropriate amount of a carrier in an organic solvent to form an internal organic phase solution; adding the internal organic phase solution into an external aqueous solution to form a mixture; and homogenizing the mixture to obtain *Adansonia digitata* nanoparticles encapsulated with a carrier. The carrier can be Gum arabic. The organic solvent can include at least one of methanol, ethanol, dichloromethane and chloroform. The external aqueous solution can include water and polyvinyl alcohol. A ratio of *Adansonia digitata*: Gum arabic:PVA can be 1:5:3; w/w/w. The mixture can be homogenized at a speed of about 22,000 rpm for about 25 minutes to form carrier encapsulated *Adansonia digitata* nanoparticles. The encapsulated *Adansonia digitata* nanoparticles isolated from the ethanol and dried. The resulting nanoparticle powder can have an average size of about 90 nm to about 100 nm, e.g., 93 nm.

Gum arabic, also known as acacia gum, is a natural gum including the hardened sap of various species of the acacia tree that grow in semi-arid land across sub-Saharan Africa. It is a complex heteropolysaccharide with a highly ramified structure, and the main chain is formed of d-galactopyranose units joined by β-d glycosidic bonds. This gum is widely used for encapsulating material, e.g., microencapsulation, by spray drying, mainly because of its emulsifying capacity and low viscosity in aqueous solution.

An effective amount of the *Adansonia digitata* nanoparticles or encapsulated *Adansonia digitata* nanoparticles can be administered to a patient in need thereof for treating and/or preventing cancer. The patient can be human or animal. The cancer can be, for example, colon cancer or breast cancer.

The present technology, thus generally described, will be understood more readily by reference to the following examples, which is provided by way of illustration and is not intended to limit the scope of the present technology.

Example 1

Synthesis of *Adansonia digitata* Nanoparticles in Methanol

Figure 1A:
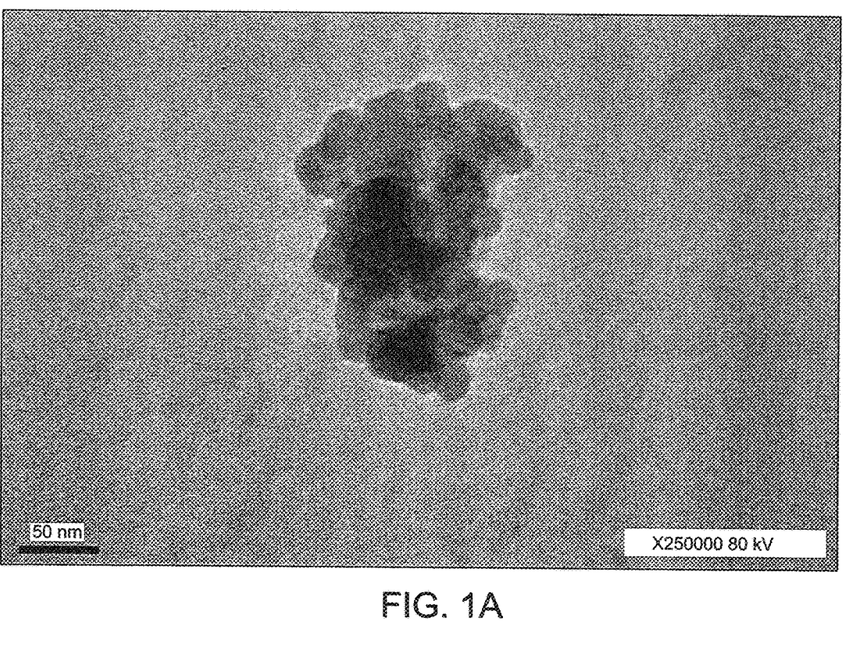
FIGS. 1A-1C show transmission electron microscopy (TEM) images of *Adansonia digitata* nanoparticles prepared according to Example 1.
Figure 1B:
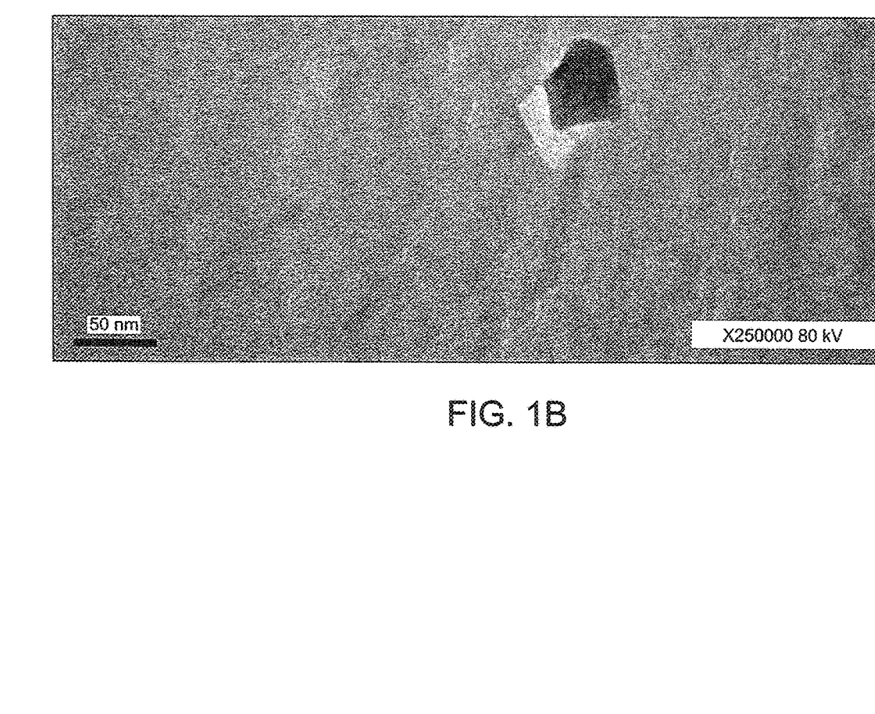
Figure 1C:
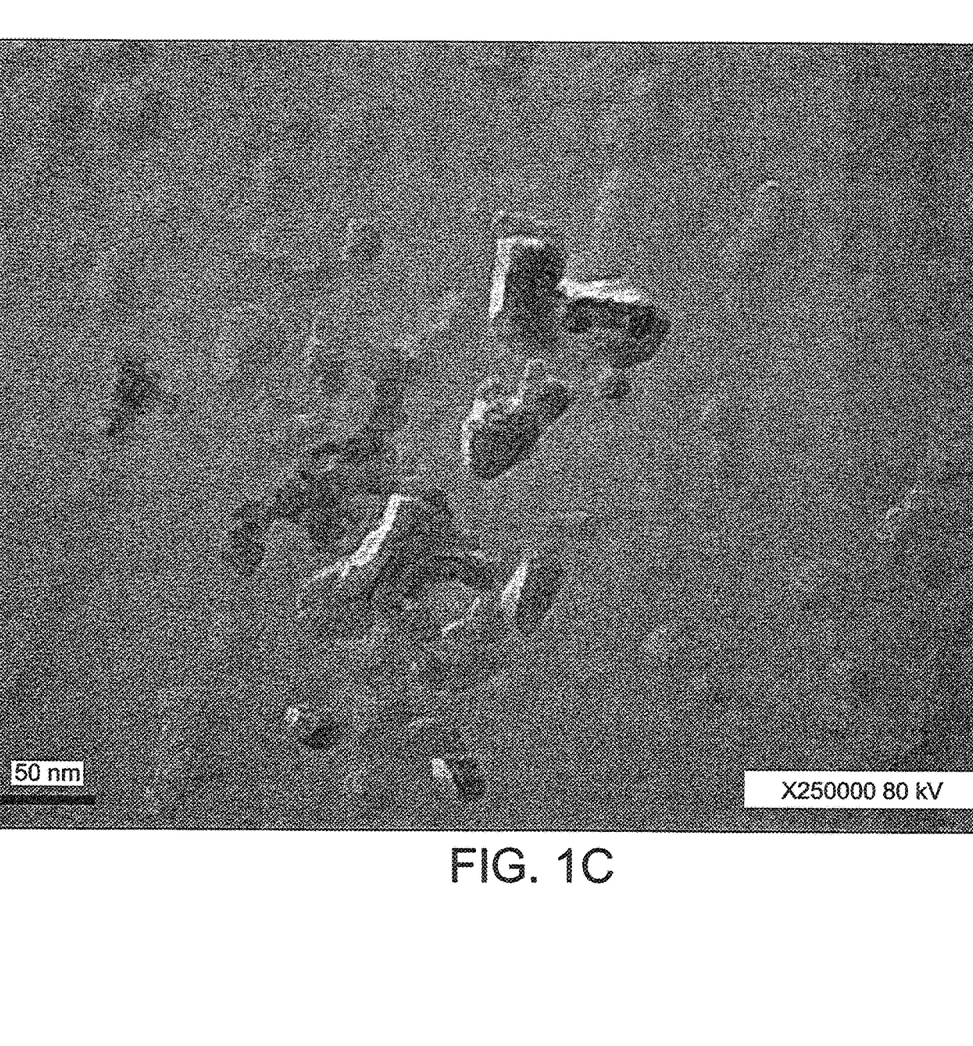
Figure 2A:
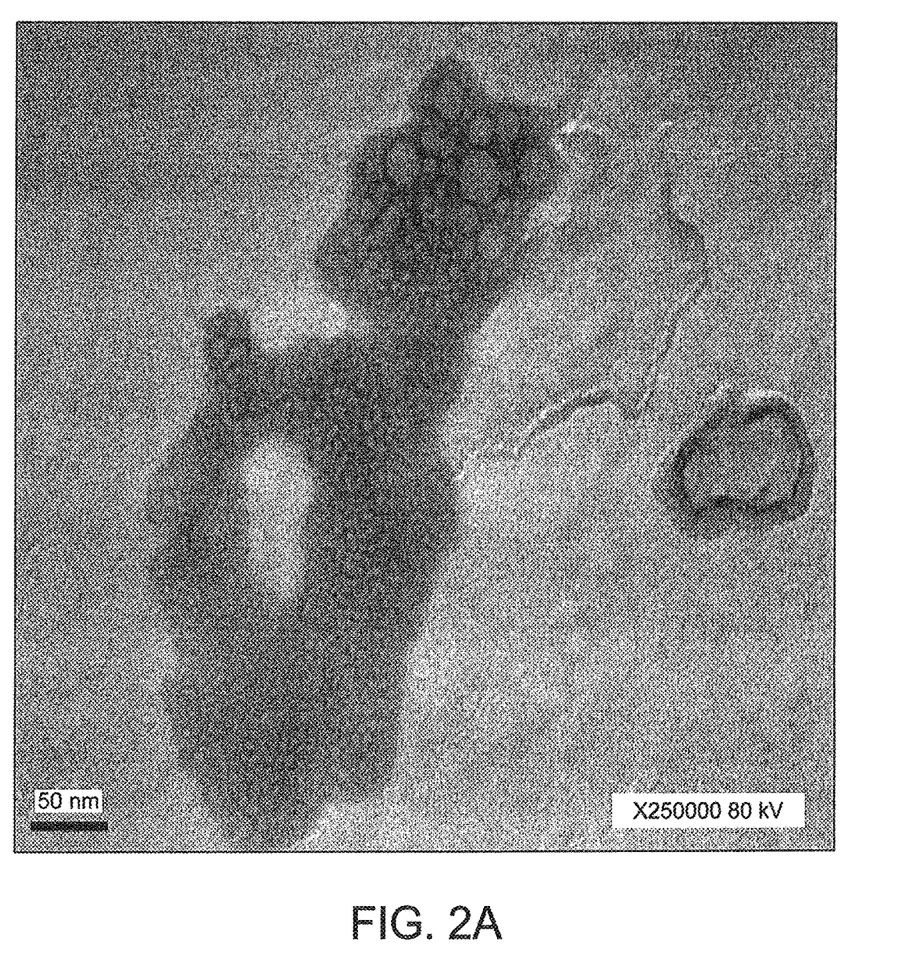
FIGS. 2A-2E show transmission electron microscopy (TEM) images of encapsulated *Adansonia digitata* nanoparticles prepared according to Example 2.
Figure 2B:
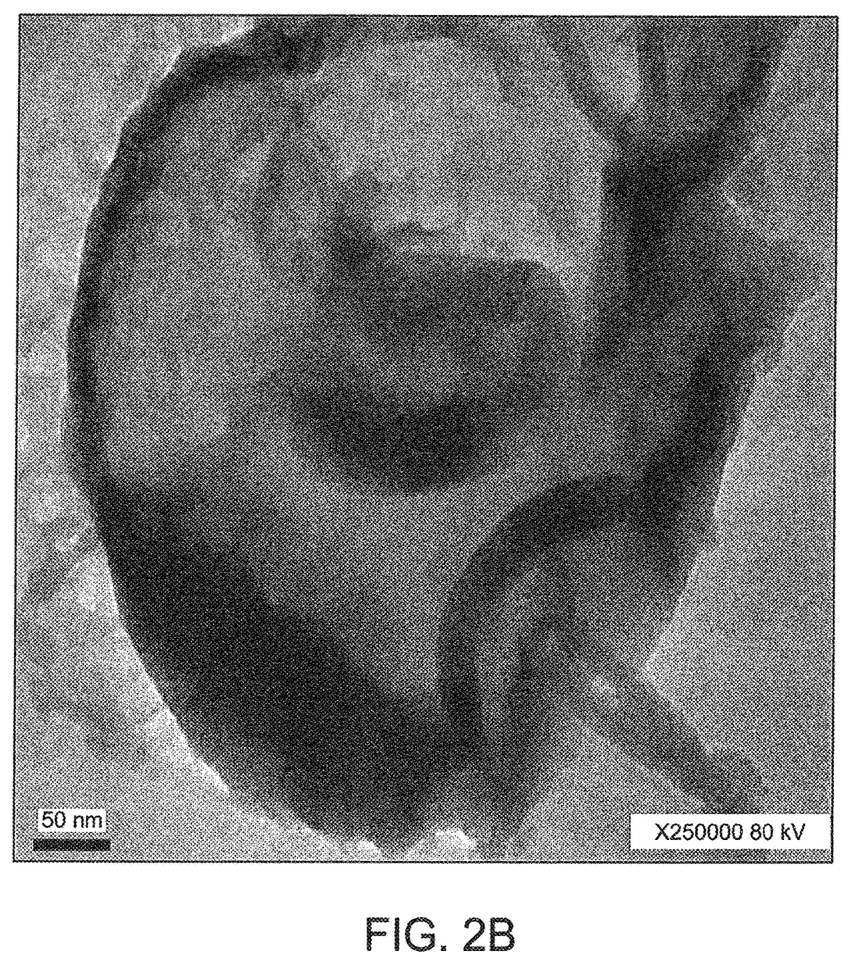
Figure 2C:
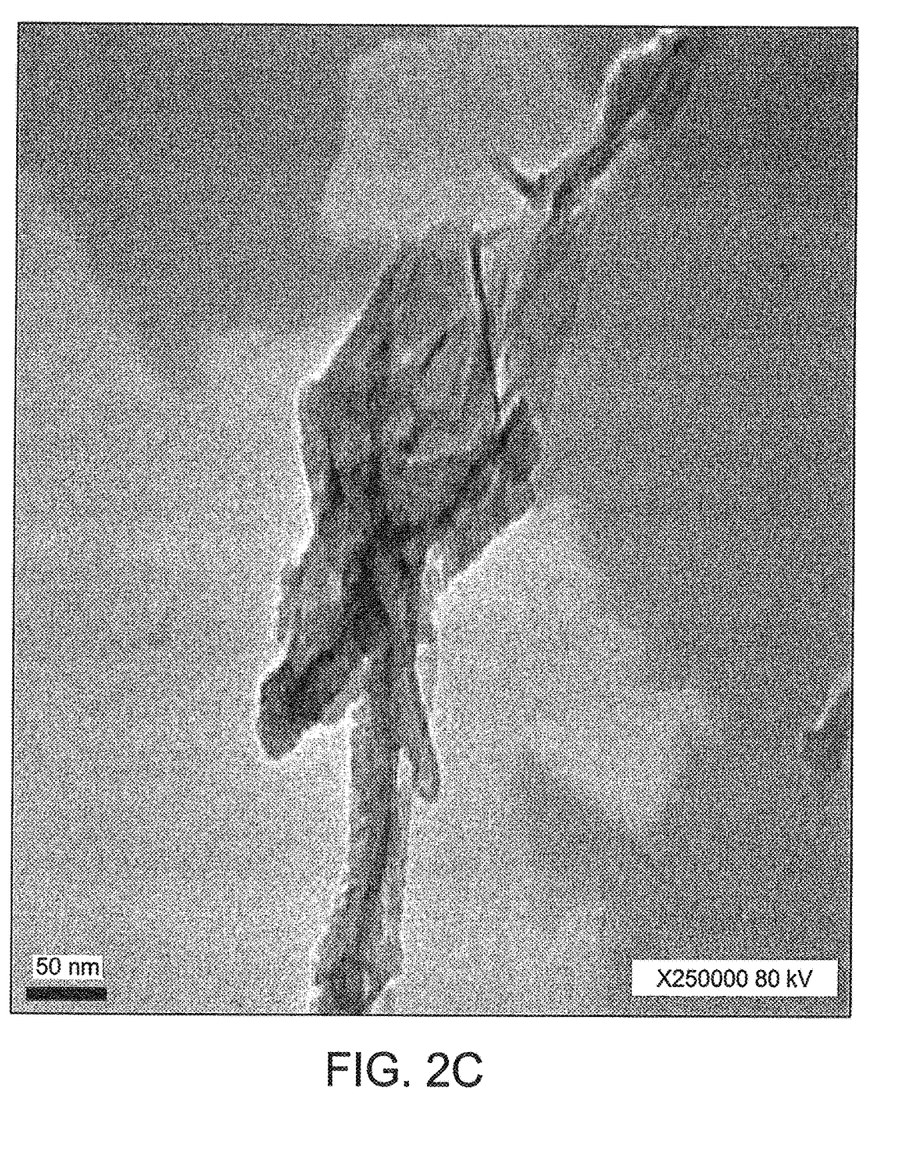
Figure 2D:
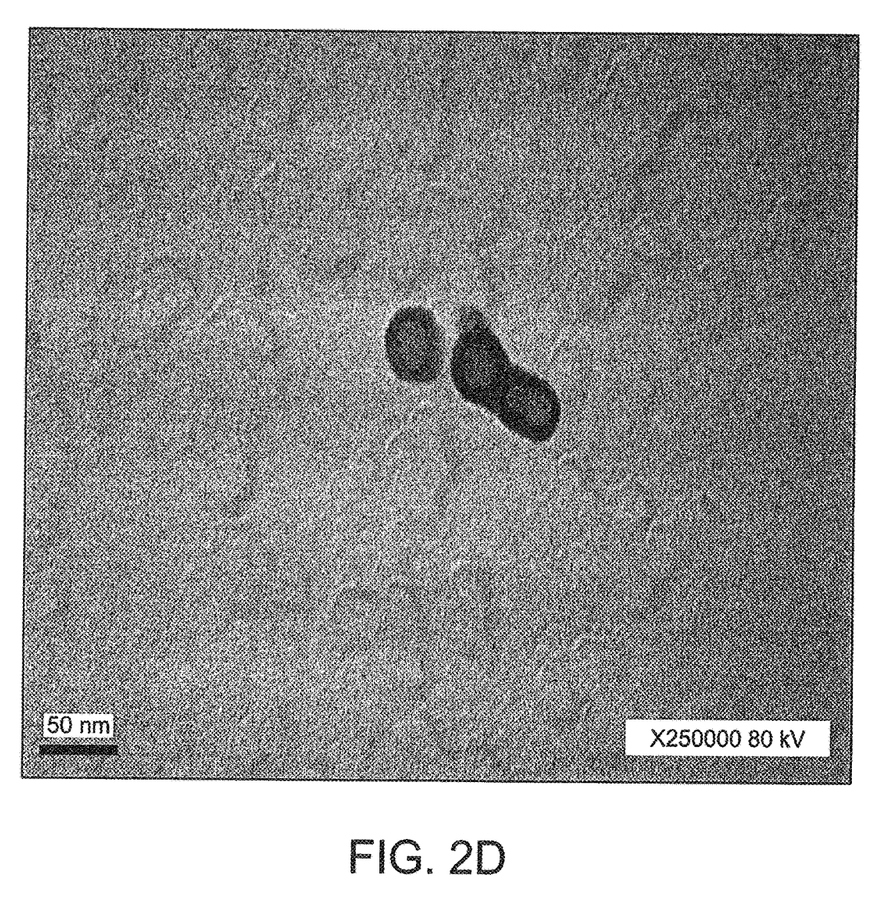
Figure 2E:
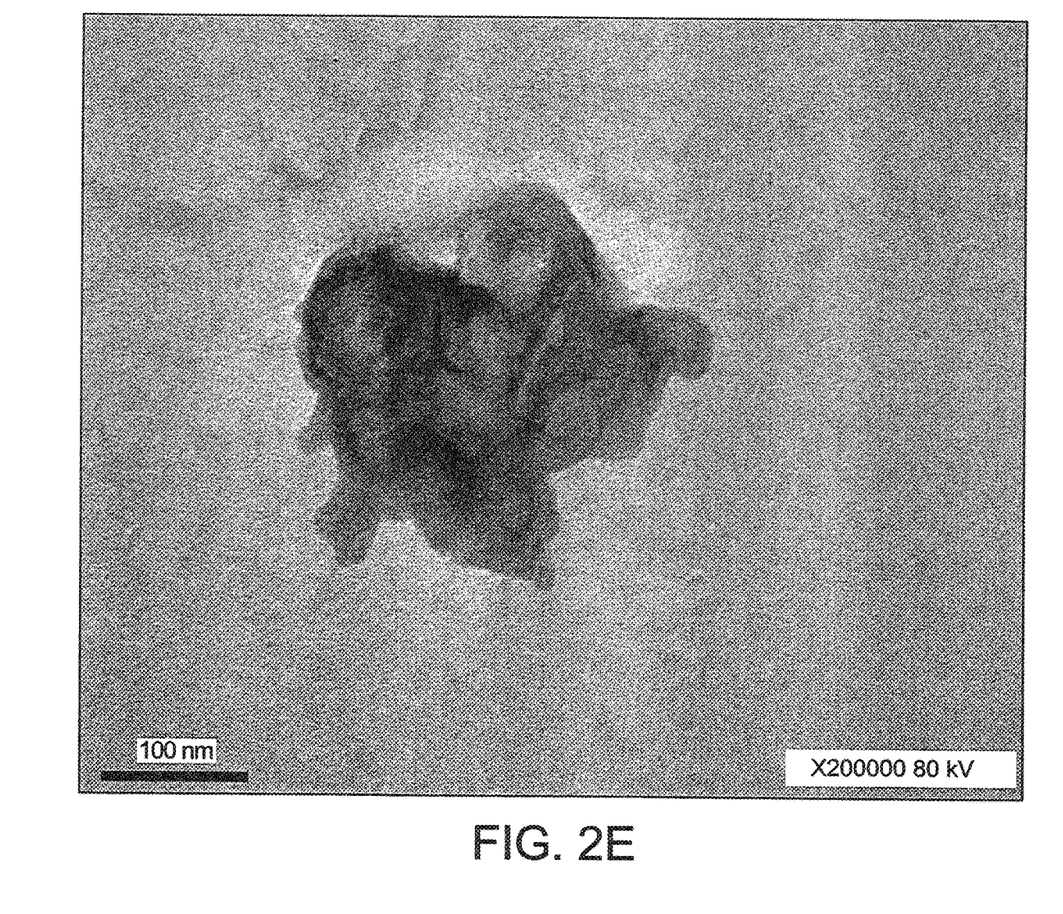
Figure 3:
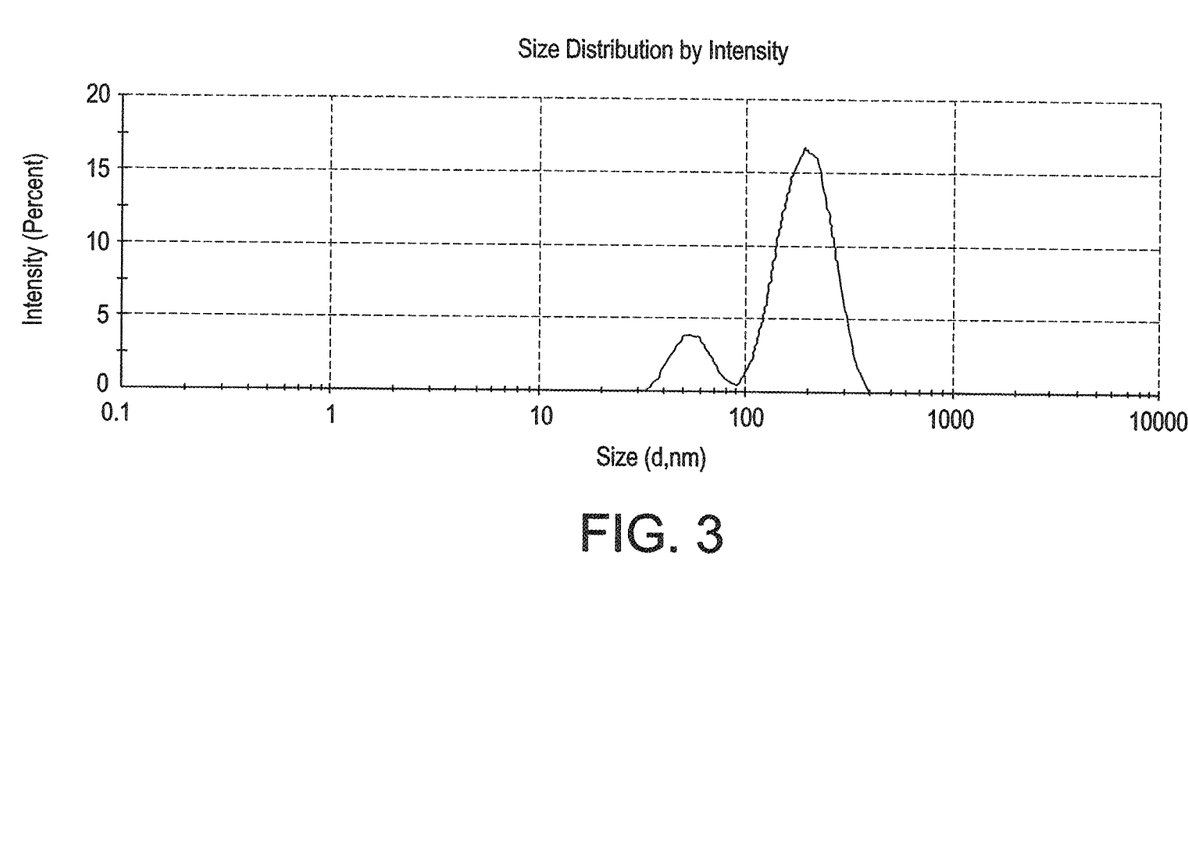
FIG. 3 shows a graph of Zeta sizer for measuring the average particle size of the *Adansonia digitata* nanoparticles prepared according to Example 1.

For the formation of *Adansonia digitata* nanoparticles, (200 mg) of *Adansonia digitata* fruit powder was taken in methanol (30 mL), and 3 mL of this solution was sprayed into boiling water (100 mL) dropwise with a flow rate of 0.2 mL/min in 5 min under ultrasonic conditions, with an ultrasonic power of 100 W and a frequency of 30 kHz. After sonication for 30 min, the contents were stirred at 200-800 rpm at room temperature for about 10 min, and then dried, to obtain *Adansonia digitata* nanoparticles beige powder with a particle size of 230.2 nm. FIGS. 1A-C show transmission electron microscopy (TEM) (JEM-1011, JEOL, Japan) images of *Adansonia digitata* nanoparticles obtained from the method of Example 1. FIG. 3 shows a graph of Zeta sizer (ZEN 3600, MALVERN, United Kingdom) for measuring the average particle size of the *Adansonia digitata* nanoparticles.

Example 2

Synthesis of Encapsulated *Adansonia digitata* Nanoparticles

Figure 4:
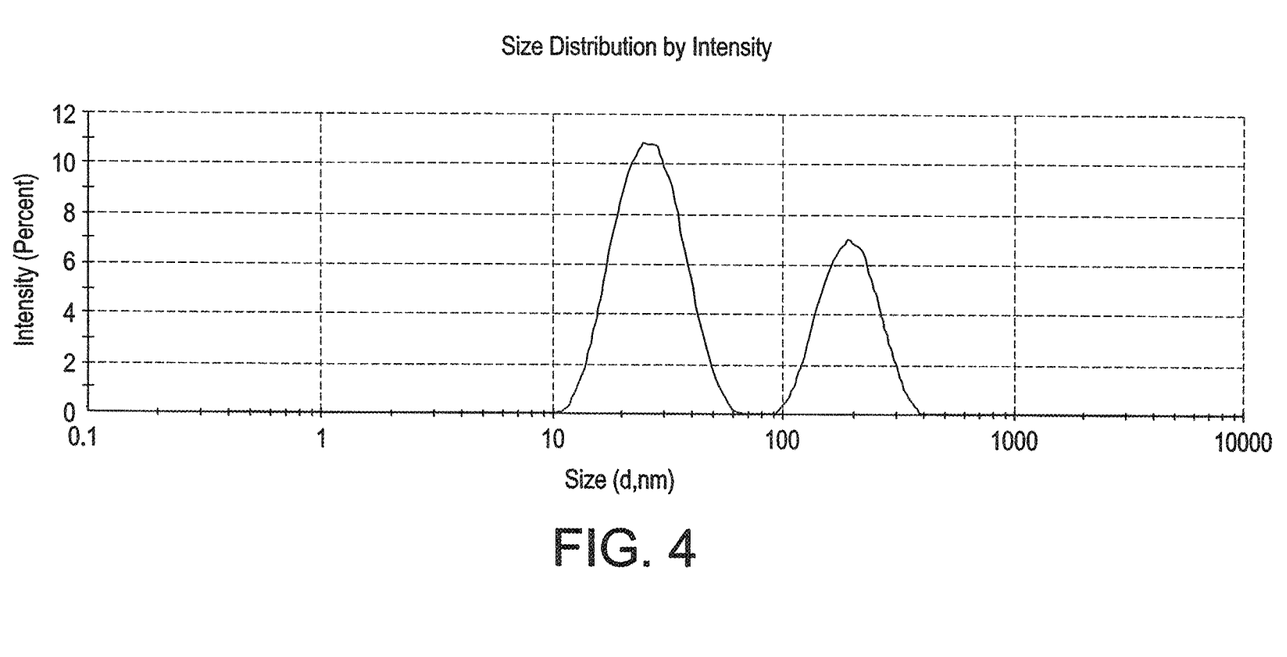
FIG. 4 shows a graph of Zeta sizer for measuring the average particle size of the encapsulated *Adansonia digitata* nanoparticles prepared according to the method in Example 2.

The nano precipitation technique (Bilati et al., 2005; Zili et al., 2005) was used for the formation of a nanoparticle encapsulation system with weight ratio *Adansonia digitata*: gum arabic:PVA (1:5:3; w/w/w). An amount of 100 mg of *Adansonia digitata* and an appropriate amount of gum arabic was dissolved in 50 ml of ethanol to form an internal organic phase solution. The internal organic phase solution was quickly injected into 130 ml external aqueous solution containing the appropriate amount of PVA, and then the solution was homogenized at 22,000 rpm for 25 minutes to form encapsulated *Adansonia digitata* nanoparticles. The ethanol was completely removed, dried, and the nanoparticles powder (93.73 nm in size) was collected. FIGS. 2A-2E show transmission electron microscopy (TEM) (TEM) (JEM-1011, JEOL, Japan) images of the *Adansonia digitata* nanoparticles encapsulated gum Arabic. FIG. 4 shows a graph of Zeta sizer (ZEN 3600, MALVERN, United Kingdom) for measuring the average particle size of the encapsulated *Adansonia digitata* nanoparticles.

Example 3

Antimicrobial Activity Evaluation

The antimicrobial effect of the *Adansonia digitata* nanoparticles was evaluated against different gram positive and gram negative bacteria as well as fungi. Results of the antimicrobial effects are provided in Table 1. The test was done using the diffusion agar technique and the well diameter was 6.0 mm (100 µl was tested). The mean zone of inhibition in mm±Standard deviation beyond well diameter (6 mm) produced on a range of environmental and clinically pathogenic microorganisms.

TABLE 1

| Sample Tested microorganisms | GON [1]Extract | GON [2]NPs | GON Encapsulated [3]NPs | Standard |
|---|---|---|---|---|
| FUNGI *Aspergillus fumigatus* (RCMB 02567) | 16.0 ± 1.0 | 22.0 ± 1.0 | 22.0 ± 1.0 | Amphotericin B 21.7 ± 1.5 |
| Gram Positive Bacteria: | | | | |
| *Streptococcus pneumoniae* (RCMB 010011) | 18.0 ± 2.0 | 20.3 ± 1.5 | 21.3 ± 1.5 | Ampicillin 21.0 ± 1.0 |
| *Bacillis subtilis* (RCMB 010068) | 20.3 ± 1.2 | 24.0 ± 1.0 | 25.3 ± 1.2 | 31.3 ± 1.5 |
| Gram Negative Bacteria: | | | | |
| *Escherichia coli* (RCMB 010054) | 17.7 ± 1.5 | 24.0 ± 2.0 | 24.7 ± 0.58 | Gentamicin 20.3 ± 0.58 |

[1]GON Extract *Adansonia digitata* extract
[2]GON NPs = *Adansonia digitata* nanoparticles.
[3]GON = Encapsulated *Adansonia digitata* nanoparticles.

Example 5

Cytotoxicity Evaluation

The potential cytotoxic effect of the *Adansonia digitata* extract and synthesized *Adansonia digitata* nanoparticles was evaluated against two cell lines, namely the human Breast carcinoma cell line MCF7 and the human colon carcinoma cells HCT-116. The results achieved using *Adansonia digitata* extract are provided in Table 2. As shown in Table 2, *Adansonia digitata* extract demonstrated weak inhibitory activity against colon carcinoma cells. Under these experimental conditions, the value of $IC_{50}$=>100 µl. The results achieved using encapsulated *Adansonia digitata* nanoparticles are provided in Tables 4 and 6.

TABLE 2

Percentage of Inhibition Using *Adansonia digitata* Extract

| Sample conc. (µl) | Viability % (3 Replicates) | | | | Inhibition % | Standard Deviation (±) |
|---|---|---|---|---|---|---|
| | $1^{st}$ | $2^{nd}$ | $3^{rd}$ | Mean | | |
| 100 | 64.93 | 67.14 | 69.26 | 67.11 | 32.89 | 2.17 |
| 50 | 82.56 | 85.23 | 81.41 | 83.07 | 16.93 | 1.96 |
| 25 | 91.87 | 94.06 | 90.37 | 92.10 | 7.90 | 1.86 |
| 12.5 | 98.04 | 99.21 | 96.76 | 98.00 | 2.00 | 1.23 |
| 6.25 | 100 | 100 | 100 | 100.00 | 0.00 | 0.00 |
| 3.125 | 100 | 100 | 100 | 100.00 | 0.00 | 0.00 |
| 0 | 100 | 100 | 100 | 100 | 0.00 | |

The results achieved using *Adansonia digitata* nanoparticles are provided in Tables 3 and 4. Table 3 shows the inhibitory activity against colon carcinoma cells. Under these experimental conditions, the value of $IC_{50}$=73.6 µl.

TABLE 3

| Sample conc. (μl) | Viability % (3 Replicates) | | | | Inhibition % | Standard Deviation (±) |
|---|---|---|---|---|---|---|
| | $1^{st}$ | $2^{nd}$ | $3^{rd}$ | Mean | | |
| 100 | 23.84 | 29.13 | 31.48 | 28.15 | 71.85 | 3.91 |
| 50 | 67.23 | 71.45 | 69.74 | 69.47 | 30.53 | 2.12 |
| 25 | 89.15 | 87.48 | 90.32 | 88.98 | 11.02 | 1.43 |
| 12.5 | 94.27 | 96.39 | 97.46 | 96.04 | 3.96 | 1.62 |
| 6.25 | 98.79 | 99.14 | 100 | 99.31 | 0.69 | 0.62 |
| 3.125 | 100 | 100 | 100 | 100.00 | 0.00 | 0.00 |
| 0 | 100 | 100 | 100 | 100 | 0.00 | |

Table 4 shows the inhibitory activity against breast carcinoma cells. Under these conditions, the value of $IC_{50}=64.7$ μl.

TABLE 4

| Sample conc. (μl) | Viability % (3 Replicates) | | | | Inhibition % | Standard Deviation (±) |
|---|---|---|---|---|---|---|
| | $1^{st}$ | $2^{nd}$ | $3^{rd}$ | Mean | | |
| 100 | 26.14 | 34.26 | 32.79 | 31.06 | 68.94 | 4.33 |
| 50 | 54.47 | 61.85 | 57.43 | 57.92 | 42.08 | 3.71 |
| 25 | 81.92 | 79.04 | 76.26 | 79.07 | 20.93 | 2.83 |
| 12.5 | 92.78 | 87.19 | 85.38 | 88.45 | 11.55 | 3.86 |
| 6.25 | 98.54 | 96.27 | 94.36 | 96.39 | 3.61 | 2.09 |
| 3.125 | 100 | 98.74 | 97.21 | 98.65 | 1.35 | 1.40 |
| 100 | 26.14 | 34.26 | 32.79 | 31.06 | 68.94 | 4.33 |

The results achieved using encapsulated *Adansonia digitata* nanoparticles are provided in Tables 5 and 6. Table 5 shows the inhibitory activity against colon carcinoma cells. Under these experimental conditions, the value of $IC_{50}=34.1$ μl.

TABLE 5

| Sample conc. (μl) | Viability % (3 Replicates) | | | | Inhibition % | Standard Deviation (±) |
|---|---|---|---|---|---|---|
| | $1^{st}$ | $2^{nd}$ | $3^{rd}$ | Mean | | |
| 100 | 17.52 | 20.43 | 18.67 | 18.87 | 81.13 | 1.47 |
| 50 | 30.64 | 34.16 | 32.72 | 32.51 | 67.49 | 1.77 |
| 25 | 54.98 | 63.25 | 61.59 | 59.94 | 40.06 | 4.37 |
| 12.5 | 69.75 | 78.14 | 84.63 | 77.51 | 22.49 | 7.46 |
| 6.25 | 87.12 | 90.63 | 91.48 | 89.74 | 10.26 | 2.31 |
| 3.125 | 94.23 | 98.26 | 97.18 | 96.56 | 3.44 | 2.09 |
| 0 | 100 | 100 | 100 | 100 | 0.00 | |

Table 6 shows the inhibitory activity against Breast carcinoma cells. Under these experimental conditions, the value of $IC_{50}=18.3$ μl.

TABLE 6

| Sample conc. (μl) | Viability % (3 Replicates) | | | | Inhibition % | Standard Deviation (±) |
|---|---|---|---|---|---|---|
| | $1^{st}$ | $2^{nd}$ | $3^{rd}$ | Mean | | |
| 100 | 16.43 | 14.95 | 13.71 | 15.03 | 84.97 | 1.36 |
| 50 | 21.96 | 23.62 | 26.48 | 24.02 | 75.98 | 2.29 |
| 25 | 32.78 | 31.53 | 35.26 | 33.19 | 66.81 | 1.90 |
| 12.5 | 64.39 | 67.29 | 61.87 | 64.52 | 35.48 | 2.71 |
| 6.25 | 80.62 | 81.74 | 78.14 | 80.17 | 19.83 | 1.84 |
| 3.125 | 91.78 | 90.53 | 89.75 | 90.69 | 9.31 | 1.02 |
| 0 | 100 | 100 | 100 | 100 | 0.00 | |

It is to be understood that the present invention is not limited to the embodiments described above but encompasses any and all embodiments within the scope of the following claims.

We claim:

1. A method of synthesizing *Adansonia digitata* nanoparticles, comprising:
   dissolving *Adansonia digitata* plant powder in an organic solvent selected from the group consisting of at least one of methanol, ethanol, dichloromethane, and chloroform to form a solution;
   adding about 1 ml to about 4 ml of the solution to about 50 ml to about 100 ml of boiling water under ultrasonic conditions to form a mixture; and;
   stirring the mixture at a speed of about 200 rpm to about 800 rpm to obtain *Adansonia digitata* nanoparticles,
   wherein the ultrasonic conditions include sonication for about 10 minutes to about 20 minutes with an ultrasonic power of 100 W and a frequency of 30 kHz prior to being stirred, and
   wherein the *Adansonia digitata* nanoparticles have a mean diameter in the range of from about 50 nm to about 300 nm.

2. The method of synthesizing *Adansonia digitata* nanoparticles according to claim 1, further comprising isolating and drying the *Adansonia digitata* nanoparticles to obtain dried *Adansonia digitata* nanoparticle powder.

3. The method of synthesizing *Adansonia digitata* nanoparticles according to claim 1, wherein the *Adansonia digitata* plant powder is derived from the fruit pulp of *Adansonia digitata*.

4. The method of preparing *Adansonia digitata* nanoparticles according to claim 1, wherein the solution is added to the boiling water by spraying the solution dropwise into the boiling water at a rate of about 0.2 ml/minute in about 5 minutes.

5. The method of synthesizing *Adansonia digitata* nanoparticles according to claim 1, wherein the *Adansonia digitata* nanoparticles have spherical, spheroidal, elongated, spherical, rod-shaped, and/or faceted shapes.

* * * * *